(12) United States Patent
Haag et al.

(10) Patent No.: US 6,579,903 B2
(45) Date of Patent: Jun. 17, 2003

(54) KLAINETINS AND THEIR DERIVATIVES, METHOD FOR THEIR PREPARATION AND USE THEREOF

(75) Inventors: Sabine Haag, Friedrichsdorf (DE); Herbert Kogler, Glashütten (DE); Ziyu Li, Offenbach (DE); Laszlo Vertésy, Eppstein-Vockenhausen (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 10/000,450

(22) Filed: Dec. 4, 2001

(65) Prior Publication Data

US 2002/0103389 A1 Aug. 1, 2002

(30) Foreign Application Priority Data

Dec. 5, 2000 (DE) .......................... 100 60 677

(51) Int. Cl.[7] .......................... A61K 31/35; A61K 31/12
(52) U.S. Cl. ...................... 514/456; 514/689; 549/401; 568/331; 424/195.1
(58) Field of Search .................... 549/401; 568/331; 514/456, 689; 424/195.1

(56) References Cited

FOREIGN PATENT DOCUMENTS

WO          WO98/58913          12/1998

OTHER PUBLICATIONS

W.L. Lasswell et al., "Cytotoxic C–Benzylated Flavonoids from Uvaria Chamae", J. Org. Chem., vol. 42, No. 8, pp. 1295–1302, (1977).
C.D. Hufford et al., "Uvaretin and Isouvaretin. Two Novel Cytotoxic C–Benzylflavanones from Uvaria Chamae L.", J. Org. Chem. vol. 41, No. 7, pp. 1297–1298, (1976).
J.R. Cole et al., Uvaretin, A New Antitumor Agent from Uvaria Acuminata (Annonaceae), J. Org. Chem., vol. 41, No. 10, pp. 1852–1855, (1976).
C.D. Hufford et al., "Uvarinol: A Novel Cytotoxic Tribenzylated Flavanone from Uvaria Chamae", J. Org. Chem., vol. 44, No. 25, pp. 4709–4710, (1979).
Achenbach, H. et al., "Oxygenated pyrenes, their potential biosynthesis precursor and benzylated dihydroflavones from two african Uvaria species," Phytochemistry, vol. 44(2):359–364 (1997).
Malterud, K. et al., "Synthesis of uvaretin, and antitumour and antimicrobial flavonoid," Tetrahedron Letters, vol. 26(39):4807–4810 (1985).
Muhammad, I. et al., "Chemistry of the annonaceae, part 18, Benzylated indoles and dihydrochalcones in *Uvaria angolensis* from Tanzania," Journal of Natural Products, vol. 48(4):571–580 (1985).

Nkunya, M.H.H. et al. "Antimalarial activity of Tanzanian plants and their active constituents: the genus Uvaria," Planta Med., vol. 57:341–343 (1991).

*Remington's Pharmaceutical Sciences*, 17th Ed., pp. 1418–1419 (1985).

Yu, D–Q. "Recent works on anti–tumor constituents from Annonaceae plants in China," Pure Appl. Chem., vol. 71(6):1119–1122 (1999).

*Primary Examiner*—Amelia A. Owens
(74) *Attorney, Agent, or Firm*—Finnegan, Henderson, Farabow, Garrett & Dunner, LLP

(57) ABSTRACT

The invention relates to compounds of formula I

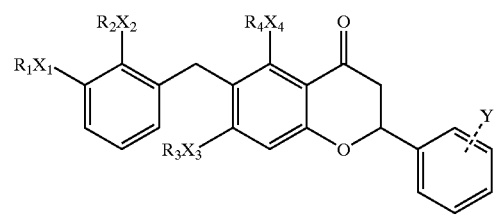

and of formula II

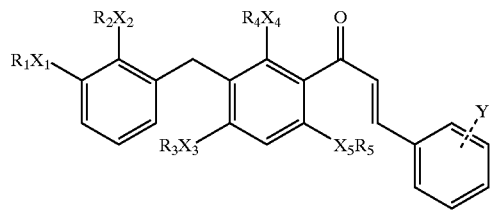

in which $R_1$, $R_2$, $R_3$, $R_4$, $R_5$, $X_1$, $X_2$, $X_3$, $X_4$, $X_5$ and Y are defined in the specification. The compounds of formulae I and II inhibit cyclin-dependent kinases (CDKS) and other kinases (KDR), have cytostatic actions, and are suitable for treating tumors. The compounds of formulae I and II are obtainable by extracting the plant *Uvaria klaineri*, PLA 100484, by cell cultures of the plant *Uvaria klaineri*, or by chemical synthesis. The invention relates to a method for preparing the compounds of formulae I and II, to the use of the compounds for producing a pharmaceutical for the treatment of malignant disorders and of diseases which may be treated by inhibition of CDKs and KDR, and also to pharmaceutical compositions comprising at least one compound of the formula I or II.

16 Claims, No Drawings

KLAINETINS AND THEIR DERIVATIVES, METHOD FOR THEIR PREPARATION AND USE THEREOF

The present invention relates to novel compounds of formula I

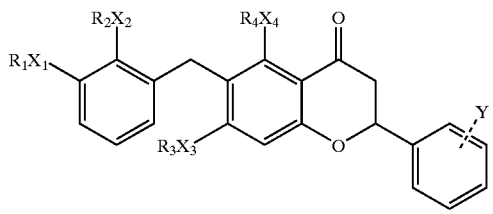

and/or of formula II

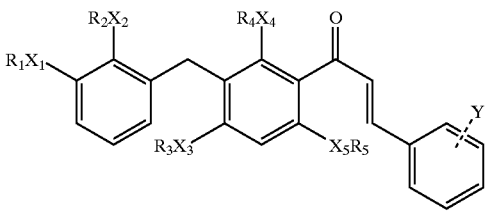

in which $R_1$, $R_2$, $R_3$, $R_4$, $R_5$, $X_1$, $X_2$, $X_3$, $X_4$, $X_5$ and Y are defined as described below. The compounds of formulae I and II inhibit cyclin-dependent kinases (CDKs) and other kinases (e.g. KDR), have cytostatic actions, and are particularly suitable for treating tumors. The compounds of formulae I and II are obtainable by extracting the plant *Uvaria klaineri*, PLA 100484, by cell cultures of the plant *Uvaria klaineri*, or by chemical synthesis. Thus, the invention relates to a method for preparing the compounds of formulae I and II, to the use of the compounds for producing a pharmaceutical for the treatment of malignant disorders and of diseases which may be treated by inhibition of CDKs and KDR, and to pharmaceutical compositions comprising at least one compound of the formulae I or II.

Cancer is a disease of humans and animals which is in most cases fatal and which is caused by the uncontrolled growth of endogenous cells. The term "cancer" denotes the formation of malignant growths (malignancies) and neoplasms (tumors or carcinomas), or the malignant degeneration and dysmaturity of white blood cells (leukemia). Cancer or tumor cells are formed by transformation of endogenous cells. The malignancy of the cancer cell expresses itself in the autonomy of growth, i.e. in its capability of growing uninhibitedly, without integration into the organ system, and infiltrating, resulting in the destruction of tissue. A sure sign of malignancy is the formation of metastases far from the tumor after hematogenic or lymphogenic spreading of tumor cells. Cancer is one of the most frequent causes of death in humans, and there is therefore a great demand for methods and agents for curing or treating malignant degenerations. In addition to the—if possible radical—surgical removal of the tumor, the options for therapy of malignant tumors include radiotherapy with X-rays, α-, β-, γ-rays, immunotherapy and chemotherapy. As yet, the use of immunotherapy is limited. Chemotherapy of tumors is understood as meaning administration of cell toxins (cytostatics) for the treatment of tumors and remaining tumor cells after local surgical treatment or irradiation. These substances intervene specifically in certain processes of cell division, so that tissues having a high proportion of dividing cells, such as rapidly growing tumor tissue, react more sensitively. The agents used are alkylating compounds, such as cyclophosphamide (The Merck Index, 12th Ed. page 463), antimetabolites, such as methotrexate (The Merck Index, 12th Ed. page 1025), alkaloids, such as vincristine (The Merck Index, 12th Ed. page 1704), antibiotics, such as daunomycin (The Merck Index, 12th Ed. page 479), and adriamycin (The Merck Index, 12th Ed. pages 581–582). However, owing to massive side-effects, all these agents have great disadvantages, so that the death of the diseased individual is only delayed, but not prevented. Furthermore, degenerated (cancer) cells become resistant to the agents used. When this occurs, the conventional pharmaceuticals no longer have any cytostatic action, but they are toxic, owing to the side-effects. Furthermore, it has been found that a combined and/or sequential use of cytostatics exceeds the activity of an individual cytostatic (monotherapy), and it is therefore possible that the considerable side-effects in polychemotherapy are non-additive. For all these reasons, novel chemotherapeutics are urgently required and thus investigated worldwide.

Surprisingly, it has been found that the African plant *Uvaria klaineri* is capable of forming highly effective novel cytostatics which inhibit cell growth even at very low concentrations. The novel compounds are denoted klainetins below and are, together with klainetin derivatives, the subject of the invention. The klainetins are substituted phenols which inhibit cyclin-dependent kinases and therefore influence cell cycle regulation. Since in cancers cell proliferation is abnormally accelerated and regulation is out of control, CDK inhibitors are valuable agents for the treatment of malignant degenerations. The compounds of formula I belong to the substituted 2,3-dihydroflavone type and the ring structure corresponds to that of isochamanetin which has been described most recently by H. Achenbach et al. in Phytochemistry, vol. 44, pages 359–364 (1997). The compounds of the formula I according to the invention are novel substituted isochamanetins.

The compounds of formula II belong to the chalcone class of compounds; the ring structure and carbon skeleton correspond to that of uvaretin. Uvaretin has been found in many Uvaria species (M. H. H. Nkunya et al., Planta Med. 57:341–343 (1991); I. Muhammad & P. G. Waterman, J. Nat. Prod. 48:571–80 (1985)). The inventive compounds of the formula II are distinguished from uvaretin by substitution and dehydrogenation and have not yet been described in the literature. Owing to their different chemical structure, the compounds of the formulae I and II have novel and physicochemical, biological and pharmacological properties. In contrast, the substances known up until now often have disadvantages which are expressed in an unsatisfactory action level, high toxicity and/or undesired side-effects.

The present invention therefore relates to compounds of formula I

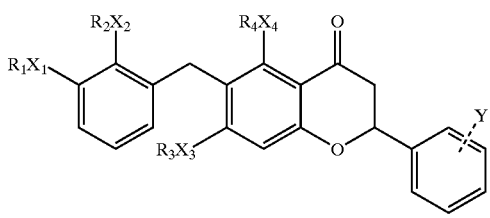

and/or of formula II

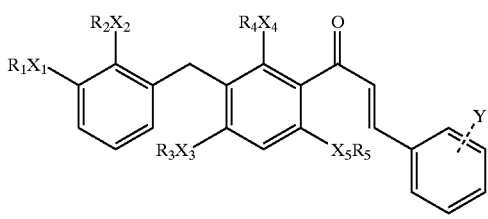

wherein
  R₁, R₂, R₃, R₄ and R₅ independently of one another are H, C₁–C₆-alkyl, C₂–C₆-alkenyl or C₂–C₆-alkynyl, unsubstituted or substituted with one or more OH;
  X₁, X₂, X₃, X₄ and X₅ independently of one another are O, NH, N—C₁–C₆-alkyl, N—C₂–C₆-alkenyl, N—C₂–C₆-alkynyl, acyl, aryl or S;
  Y is one or more H, halogen, OH, O—C₁–C₆-alkyl, O—C₂–C₆-alkenyl, O—C₂–C₆-alkynyl, NH₂, NH—C₁–C₆-alkyl, NH—C₂–C₆-alkenyl, NH—C₂–C₆-alkynyl, NH-acyl, SH, S—C₁–C₆-alkyl, S—C₂–C₆-alkenyl, S—C₂–C₆-alkynyl, acyl or aryl;
wherein the compounds may be in any stereochemical form, mixtures of said forms in any ratio, physiologically tolerated salts, and/or chemical equivalents thereof.

In the formulae I and II
  C₁–C₆-alkyl is a straight-chain or branched alkyl having 1 to 6 carbon atoms such as methyl, ethyl, isopropyl, tert-butyl and hexyl,
  C₂–C₆-alkenyl is a straight-chain or branched alkenyl having 2 to 6 carbon atoms such as allyl, crotyl and pentenyl, and
  C₂–C₆-alkynyl is a straight-chain or branched alkynyl having 2 to 6 carbon atoms such as propynyl, butynyl und pentynyl.

Aryl can be, for example, phenyl, benzyl or 1- or 2-naphthyl, which may also be unsubstituted or substituted, for example, by halogen such as chlorine, bromine and fluorine, by alkyl having 1–4 carbon atoms, preferably methyl, by hydroxyl, by alkoxy having 1–4 carbon atoms, in particular methoxy, and/or by trifluoromethoxy.

Acyl can be aliphatic or aromatic acyl radicals. Aliphatic acyl has 1–7, preferably 1–4, carbon atoms, such as formyl, acetyl, propionyl, butyryl, hexanoyl, acryloyl, crotonoyl, propioloyl, which may be further substituted, for example, by halogen such as chlorine, bromine and fluorine, by amino and/or by alkylamino having 1–4 carbon atoms, preferably methyl- or ethylamino groups. Aromatic acyl can be, for example, benzoyl or naphthoyl, which may also be further substituted, for example, by halogen such as chlorine, bromine and fluorine, by alkyl having 1–4 carbon atoms, preferably methyl, by hydroxyl, by amino groups such as ethylamino, or by alkoxy groups having 1–7, preferably 1–4, carbon atoms, in particular methoxy.

In formula I, X₁R₁, X₂R₂ and X₃R₃ preferably are OH, X₄R₄ preferably is O—C₁–C₄-alkyl and Y is H. In the formula II, X₁R₁, X₂R₂, X₃R₃, and X₄R₄ preferably are OH, X₅R₅ preferably is O—C₁–C₄-alkyl and Y is H.

The invention thus relates to klainetin A of the formula IA

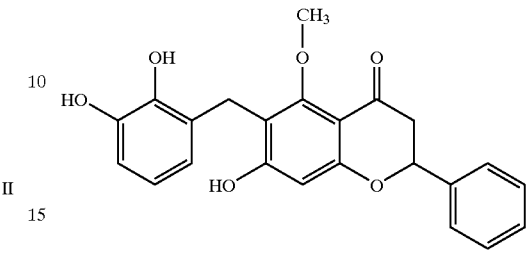

in all its stereochemical forms, to mixtures of said forms in any ratio, and to physiologically tolerated salts thereof.

The invention further relates to klainetin B of the formula IIA

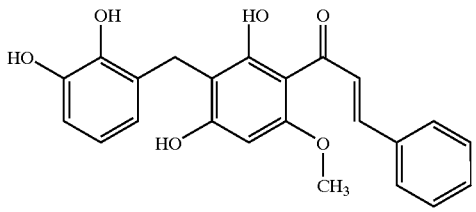

According to the invention, the compounds of the formulae I and II are obtainable by extracting the plant *Uvaria klaineri* or any of its variants or mutants under suitable conditions. The klainetins are produced by subsequent isolation of the compounds and, where appropriate, conversion into chemical derivatives and physiologically tolerated salts thereof.

The invention therefore relates furthermore to a method for preparing a compound of formulae I and/or II, which comprises culturing the plant *Uvaria klaineri* or any of its variants or mutants under suitable conditions, until one or more klainetins of formulae IA and/or IIA accumulate in the plant material, are subsequently isolated from the plant parts and, where appropriate, are converted into chemical derivatives and/or physiologically tolerated salts.

The plant *Uvaria klaineri*, its mutants and/or variants are preferably grown on suitable soil in a tropical or subtropical climate, until the novel klainetins accumulate in the plant. The novel klainetins are subsequently isolated from the plants and, where appropriate, fractionated into the individual active components.

The plants are produced preferably under tropical conditions, for example, at a temperature between 18 and 45° C. and high humidity.

The product can also be produced in cell cultures. To this end, living cells of the plant *Uvaria klaineri* are transferred into a suitable culture medium and the cell cultures are grown until the compounds of the invention accumulate in the medium. Cell cultures are prepared often from callus cultures. The culture media comprises minerals, vitamins, carbon sources such as sucrose, and nitrogen sources such as nitrogen salts. The klainetins are then isolated from the cell culture and, where appropriate, fractionated into the individual active components.

Many reactions for the chemical modification of flavones or phenols are described in the literature. The phenolic OH groups of the present compounds therefore can be derivatized using chemical reactions known in the art. It is, for example, possible to achieve reduction to the saturated compounds catalytically with hydrogen or to reduce carbonyl groups using metal hydrides auch as aluminum hydrides or borohydrides. Another suitable example is the reaction of carbonyl groups with hydroxylamine or its derivatives to give the oximes which can be chemically converted further.

The invention is described in detail below, in its several embodiments.

The klainetins of the invention are produced by *Uvaria klaneri. Uvaria klaineri* is a widespread evergreen liana of the Annonaceae family. The Annonaceae family includes many tropical useful and medicinal plants. Their geographical range is the entire tropics; the sample from which the klainetins were isolated was collected in Gabon, specifically in the area around Rabi/Gamba.

When isolating klainetins, it is possible to use other species from the genus Uvaria or from plants of the same species which come from a different location. Klainetin content and composition may vary depending on the conditions at the location, such as soil quality, temperature, humidity, and incidence of light.

The method of the invention may be used for extraction and isolation on a laboratory scale (100 g to 1 kg of dry plant material) and on an industrial scale (100 to >1000 kg).

*Uvaria klaineri* generates a mixture of klainetins in the plant material. Depending on the harvest of the plant and its parts, the quantitative proportion of one or more of the klainetins of the invention may vary. In addition, it is possible to control the synthesis of individual klainetins via the growth conditions so that one or more of the klainetins fail to be generated or are generated in an amount below the detection limit.

The plant material preferably contains a detectable klainetin. Preference is given to the formation of klainetins A and B.

In addition to klainetins A and B (compounds of the formulae IA and IIA, respectively), the plant *Uvaria klaineri* also generates further related compounds which are distinguished from the compounds represented by the formulae IA and IIA by altered hydroxylation or glycosylation. For example, a klainetin with a molecular mass of 408 Da was detected as by-product.

The plants may be cultured outdoors or, preferably, in a greenhouse. Alternatively, it is possible to use plant cell cultures for producing the metabolites. Normally, the starting material is callus cultures. Selection of suitable bioreactors for growing the plant cell culture makes it possible to achieve optimal mixing and airing of the culture without disturbing the plant cells, cell growth and metabolite production. The cultures may be mixed using, for example, airlift reactors or bubble column reactors, or blade or propeller stirrers. The cells can grow as individual cells or as branched or unbranched cell aggregates or cell chains. Metabolite production can be induced by stimulation with exogenous factors, for example heavy metal salts or plant elicitors.

Product formation in the plant can be monitored on the basis of the pH of the cultures and by chromatographic methods such as thin layer chromatography, high pressure liquid chromatography, or by testing the biological activity. The klainetins of the invention are contained both in the leaves and in other parts of the plant. The isolation method described below serves to purify the klainetins of the invention, preferably to purify klainetins A and B.

The klainetins of the invention were isolated and purified from the plant or the culture medium according to known methods with respect to the chemical, physical and biological properties of the natural substances. The klainetin concentrations in the starting material or in the individual isolation stages can be assayed by thin layer chromatography, for example, on silica gel with chloroform/methanol/glacial acetic acid/water mixtures (e.g. in a quantitative 8:1:1:0.2 ratio) as the mobile phase, or HPLC. For thin layer chromatography fractionation, detection can be carried out, for example, using color reagents such as $I_2$ vapor, iron(III) chloride, vanilline-$H_2SO_4$ or Pauli's reagent (sulfanilic acid, diazotized), the amount of the substance formed being. compared with a standard solution.

The klainetins of the invention are isolated by harvesting the plant, i.e., by collecting the leaves, stems, wood, bark or roots, and then by extracting the plant, which preferably is still fresh or is dried according to the conventional methods. Next, the klainetins are extracted from the plant material, optionally with a water-containg organic solvent. The organic solvent phase contains the klainetins of the invention, which are, where appropriate, concentrated in vacuo and further purified, as described below.

The extracts are combined, diluted with water, and extracted with a suitable organic solvent immiscible with water, for example n-butanol. The subsequently removed organic phase is, where appropriate, concentrated in vacuo. Lipids can be removed from the product of interest by diluting the concentrate with a nonpolar solvent in which the klainetins of the invention have very low solubility, such as hexane, petroleum ether, or diethyl ether. Here, the kainetins precipitate, and the lipophilic contaminants such as waxes remain in solution and are removed by conventional solid/liquid phase separations. The precipitate which contains all klainetins is dissolved in water/methanol in 1/30 of the original volume. The precipitate is dissolved in the process and is lyophilized. The lyophilisate, denoted "crude product" below, contains 0.5 to 10% klainetins and is used for further isolation.

One or more of the klainetins of the invention are further purified by chromatography on suitable materials, for example, on molecular sieves, on normal phase supports such as silica gel and aluminum oxide, on ion exchange materials, on adsorber resins, or on reversed phase (RP) materials. The klainetins are separated with the aid of said chromatography. Klainetin chromatography is carried out with buffered aqueous solutions or mixtures of aqueous and organic solutions.

The term "mixtures of aqueous and organic solutions" means all organic solvents miscible with water, for example, methanol, 2-propanol and acetonitrile, at a concentration of from 10 to 80% solvent, preferably 15 to 55%, solvent, or else all buffered aqueous solutions which are miscible with organic solvents. The buffers to be used are the same as those mentioned above.

The klainetins are separated due to their different polarity with the aid of reversed phase chromatography, for example on MCI® (adsorber resin from Mitsubishi, Japan) or Amberlite XAD® (TOSOHAAS), on other hydrophobic materials, for example, on RP-8 or RP-18 phases, or else on "polyamides". In addition, the separation may be carried out with the aid of normal phase chromatography, for example on silica gel, aluminum oxide and the like.

Klainetin chromatography is carried out with buffered or acidified aqueous solutions or mixtures of aqueous solutions with alcohols or other organic solvents miscible with water. The organic solvents usually used are propanol and acetonitrile.

The term "buffered or acidified aqueous solutions" means, for example, water, phosphate buffer, ammonium acetate, citrate buffer at a concentration of from 1 mM to 0.5 M, and also formic acid, acetic acid, trifluoroacetic acid and all commercially available acids known to the skilled worker, at a concentration of from 0.01 to 3%, generally, 0.1%.

Chromatography is carried out using a gradient which starts with 100% aqueous buffer and ends with 100% solvent; preference is given to running a linear gradient of 10 to 50% 2-propanol or acetonitrile.

Alternatively, it is also possible to carry out gel chromatography or chromatography on hydrophobic phases.

Gel chromatography is carried out on polyacrylamide gels or mixed polymer gels such as Biogel-P 2® (Biorad), Fractogel TSK HW 40® (Merck, Germany or Toso Haas, USA), or on Sephadex® (Pharmacia, Uppsala, Sweden).

The order of the abovementioned chromatographies is reversible.

Another very effective purification step for klainetins is crystallization. The klainetins crystallize from solutions in organic solvents and from mixtures of water with organic solvents. Crystallization is carried out in a manner known in the art, for example by concentrating or cooling saturated klainetin solutions.

The klainetins of the invention are stable in the solid state and in solutions having a pH in the range between 3 and 8, in particular 4 and 6, and can thus be worked into customary pharmaceutical preparations.

The klainetins and derived chemical derivatives of the formulae I and II can be converted into the corresponding physiologically tolerated salts according to methods known to the skilled worker.

The term "physiologically tolerated salts" of compounds of the formulae I and II means both organic and inorganic salts thereof, as described in Remington's Pharmaceutical Sciences (17th edition, page 1418 (1985)). Owing to their physical and chemical stability and to solubility, sodium, potassium, calcium and ammonium salts, are *inter alia* preferred for acidic groups; salts of hydrochloric acid, sulfuric acid, phosphoric acid or of carboxylic acids or sulfonic acids, such as acetic acid, citric acid, benzoic acid, maleic acid, fumaric acid, tartaric acid and p-toluenesulfonic acid, are *inter alia* preferred for basic groups.

The invention furthermore includes obvious chemical equivalents of the compounds of the formulae I and II, which are slightly different chemically, i.e. they have the same effectiveness or can be converted into the compound of the invention under mild conditions. Said equivalents include, for example, esters and ethers and also reduction products of the compounds of the invention.

Ester and ether derivatives and reduction products can be prepared according to methods described in the literature, for example in Advanced Organic Synthesis, 4th edition, J. March, John Wiley & Sons., 1992.

The present invention includes all stereoisomeric forms of the compounds of the formulae I and II. Asymmetry centers contained in the compounds of the formulae IA and IIA may all have, independently of one another, either S configuration or R configuration. The invention includes all possible enantiomers and diastereoisomers and likewise mixtures of two or more stereoisomeric forms, for example mixtures of enantiomers and/or diastereoisomers, at all ratios. The invention thus relates to enantiomers in enantiomerically pure form, both as levorotatory and dextrorotatory antipodes, R and S configurations, in the form of racemates and in the form of mixtures of the two enantiomers at all ratios. If cis/trans isomerism is present, the invention relates to both the cis and the trans form and to mixtures of these forms at all ratios. Assays for determining biological klainetin activities:

The assay systems comprise a kinase of the CDK family, CDK4 (cyclin-dependent kinases), and KDR (tyrosine kinase receptor), which play an important part in cell cycle regulation and angiogenesis. Through phosphorylation reactions, CDK4 initiates a reaction cascade at the end of which the cell cycle progresses from the G1 phase to the S phase. Thus, further cell division and further unregulated cell growth can be stopped if this key enzyme is inhibited. KDR is a tyrosine kinase receptor which plays a key part in endothelium growth and angiogenesis and is likewise involved in tumor formation. Thus, CDK4 and KDR represent important therapeutic target molecules for cancers and other proliferative disorders. The assay involves measuring CDK4 and KDR kinase activities on the basis of phosphorylation of a specific peptide substrate. In addition to the inhibiting activity on the kinases mentioned, other kinases which are involved in the formation of cancer and in the inflammation cascade were also inhibited by the klainetins.

Owing to their valuable pharmacological properties, the compounds of the invention are suitable for specific application as pharmaceuticals in human and/or veterinary medicine. The compounds of the invention may be used for cancers, in particular as chemotherapeutics. Due to their cytostatic properties, in particular their strong antitumor activity, and also to an antimicrobial action, they may be used in particular as cytostatics for malignant degenerations in animals and humans.

In tumor cells which have developed resistances against conventional agents, only novel agents have a therapeutically sufficient action. Thus, the klainetins of the invention and chemical derivatives thereof of formulae I and II potentially have an outstanding action even against these problem cell types.

The invention also relates to pharmaceutical preparations which contain one or more of the klainetins of the invention and/or chemical derivatives thereof. Preference is given to their use in a mixture with suitable excipients or carrier material. Carrier materials which may be used in humans are all pharmacologically acceptable carrier materials and/or excipients.

The invention also relates to a method for preparing a pharmaceutical of the invention which comprises combining at least one of the compounds of the invention with a pharmaceutically suitable and physiologically tolerated carrier and, where appropriate, with further suitable active substances, additives or excipients, into a form that can be administerated suitably.

The pharmaceuticals of the invention are generally administered orally, locally or parenterally, but rectal administration is in principle also possible. Suitable solid or liquid pharmaceutical preparation forms are, for example, granules, powders, tablets, coated tablets, capsules, microcapsules, suppositories, syrups, emulsions, suspensions, aerosols, drops or injectable solutions in ampoules and/or preparations with protracted active substance release. Production of these preparations usually involves using carriers and additives and/or aids such as disintegrants, binders, coating agents, swelling agents, glidants or lubricants, flavorings, sweeteners or solubilizers. Frequently used carriers or excipients include magnesium carbonate, titanium dioxide, lactose, mannitol and other sugars, talc, lactalbumin, gelatin, starch, vitamins, cellulose and its derivatives, animal or vegetable oils, polyethylene glycols and solvents such as sterile water, alcohols, glycerol and polyhydric alcohols.

It is possible, where appropriate, to microencapsulate the dosage units for oral administration in order to delay the release or to prolong it over a longer period, for example by coating or by embedding the active substance in particle from in suitable polymers, waxes or the like.

Preference is given to producing and administering the pharmaceutical preparations in dosage units, each unit containing as the active ingredient a particular dose of one or more compounds of the klainetins of the invention and/or chemical derivatives thereof. For solid dosage units such as tablets, capsules and suppositories, said dose may be up to about 500 mg, but is usually about 0.1 to 200 mg, and for injection solutions in ampoules up to about 500 mg, but usually about 0.1 to 100 mg, per day.

The daily dose to be administered depends on the body weight, age, sex and state of the patient. However, higher or lower daily doses may also be appropriate under certain circumstances. The daily dose may be administered both by a single administration in the form of a single dosage unit or else in several smaller dosage units and by multiple administrations of subdivided doses in particular intervals.

The invention is further illustrated by the following examples. Percentages relate to weight. Mixing ratios of liquids relate to volume unless otherwise indicated.

EXAMPLE 1

Preparation of a Primary Extract of *Uvaria Klaineri*

Leaves of *Uvaria klaineri* were collected in a fresh state and were then air-dried at approx. 40° C. After drying, 100 g of dry material were ground and extracted with stirring with 1 liter of methanol at 40° C. for 8 h. After finishing extraction, the plant debris was removed by filtration and the methanolic extract was evaporated in vacuo to near dryness. The residue was resuspended again in a little water and then freeze-dried. The primary extract produced in this way was kept at 4° to −20° C. and used for further isolation, as described in Example 3. The biological activity was assayed by removing tannins and other strongly hydophilic or lipophilic interfering substances by means of chromatography on polyamide and on polystyrene adsorber resin.

EXAMPLE 2

Plant Production: Collecting the Seeds, Sowing, Growth Conditions and Harvest Conditions

*Uvaria klaineri* seeds were collected after maturation and sowed for further cultivation of the plants in a greenhouse. The optimal temperature was approx. 28° C. at 70–90% humidity. The plants were cultured for from several weeks to:months, usually for about 4–6 months, until the leaves were harvested.

EXAMPLE 3

Isolation of the Klainetin Mixture From the Plant *Uvaria Klaineri*

After harvesting *Uvaria klaineri*, 200 g of dried leaves, obtained according to Example 1, were crushed in a grinder, stirred with 2 liters of methanol for 16 hours and then filtered. The active substance-containing methanolic solution was concentrated in vacuo; the dry mass was 3.05 g. The concentrate was applied to a prepacked column containing 412 ml of ®MCI GEL, CHP20P. Elution took place using a gradient of 10% acetonitrile in water after 90% acetonitrile in water. The column flow-through (50 ml per minute) was collected in fractions (50 ml each) and the klainetin-containing fractions 31 and 32 (klainetin A) and 51–56 (klainetin B) were combined. Concentration in vacuo and freeze-drying yielded 26 mg (klainetin A crude product) and 70 mg (klainetin B crude product) of a brown powder.

EXAMPLE 4

Purification of the Klainetin a Component on Reverse Phase RP-18.

®Superspher 100 RP-18 e (E. Merck, Darmstadt) was introduced into a 19.7 ml preparative HPLC column (1 cm (ID)×25 cm H) and the 26 mg of klainetin A crude mixture, obtained according to Example 3, was applied. Elution was carried out with 30% acetonitrile in 0.01 M aqueous ammonium acetate solution, pH 7, after the loaded column has been washed beforehand with 140 ml of 25% acetonitrile in water and then with 60 ml of 30% acetonitrile in water. The column flow-through was 10 ml/minute, and fractions of 10 ml were collected. Klainetin A is present in fractions 25 and 26. After concentration in vacuo and freeze-drying, 9.8 mg of klainetin A of >97% purity were obtained:

ESI+MS: 393.4 Da(M+H)$^+$, 431.2 Da(M+K)$^+$; ESI−MS: 391.5 Da(M−H)$^-$

EXAMPLE 5

Characterization of Klainetin A

Appearance: light yellow substance, soluble in polar organic solvents but only slightly soluble in water. The compound was stable in a neutral and mildly acidic environment but unstable in the alkaline and strongly acidic range. UV maxima: 207, 286, 318 (Sh) nm in water/acetonitrile (8:2), pH 2 and 253, 288 (Sh) and 325 nm in water/acetonitrile (8:2) at pH 7.

High-resolution mass spectrometry found the following molecular mass for (M+H)$^+$: 393.13394 Da, corresponding to the klainetin A molecular formula of $C_{23}H_{20}O_6$. Electron spray ionization (ESI, positive) produced by means of MS/MS fragmentation the following ions: 393, 289, 283, 271, 131 and 123 Da. Electron spray ionization (ESI, negative) produced by means of MS/MS fragmentation the following ions: 391, 269 and 109 Da.

NMR Signals: See Table 1

TABLE 1

NMR chemical shifts of klainetin A, c = 2 mg/ml, 300 K in DMSO

| Position | δ ($^{13}$C) | m ($^{13}$C) | δ ($^1$H) | $^n$J$_{CH}$ | $^n$J$_{HH}$ |
|---|---|---|---|---|---|
| 2 | 77.46 | d | 5.448 | 7.33, 2.869 | 2.867, 2.771 |
| 3 | 44.59 | t | 2.867, 2.771 | — | 5.448 |
| 4 | 187.62 | s | — | 2.867, 2.771, 5.448 | — |
| 4a | 104.37 | s | — | 6.17 | — |
| 5 | 159.97 | s | — | 6.17, 3.747 | — |
| 5-OMe | 55.30 | q | 3.747 | — | — |
| 6 | 106.44 | s | — | 6.17, 3.747 | — |
| 7 | 161.60 | s | — | 3.747 | — |
| 7-OH | — | — | ? | — | — |
| 8 | 92.99 | d | 6.17 | — | — |
| 8a | 162.88 | sbr | — | — | — |
| 9 | 139.41 | s | — | 2.869, 5.448, 7.34, 7.30 | — |
| 10 2C | 125.85 | d | 7.33 | 7.33, 7.30, 5.448 | (7.34) |
| 11 2C | 128.32 | d | 7.34 | 7.34 | (7.30, 7.33) |
| 12 | 127.87 | d | 7.30 | 7.33 | 7.34 |
| 13 | 22.15 | t | 3.75 | 6.17 | — |
| 14 | 127.52 | s | — | 3.75, 6.43 | — |

TABLE 1-continued

NMR chemical shifts of klainetin A, c = 2 mg/ml, 300 K in DMSO

| Position | δ ($^{13}$C) | m ($^{13}$C) | δ ($^1$H) | $^n$J$_{CH}$ | $^n$J$_{HH}$ |
|---|---|---|---|---|---|
| 15 | 142.93 | s | — | 6.174, 6.566, 3.757 | — |
| 16 | 144.61 | s | — | 6.428 | — |
| 17 | 112.58 | d | 6.566 | 6.174 | 6.428 |
| 18 | 118.16 | d | 6.428 | — | 6.566, 6.174 |
| 19 | 118.43 | d | 6.174 | 6.566, 3.757 | 6.428 |

EXAMPLE 6

Purification of the Klainetin B Component on Reverse Phase RP-18

®Supersher 100 RP-18 e (E. Merck, Darmstadt) was introduced into a 19.7 ml preparative HPLC column (1 cm (ID)×25 cm H) and the 70 mg of klainetin B crude mixture, obtained according to Example 3, was applied. Elution was carried out with a gradient of 35% acetonitrile in 0.01 M aqueous ammonium acetate solution, pH 7.3, after 50% acetonitrile in aqueous ammonium acetate solution, pH 7.3. The column flow-through was 10 ml/minute, and fractions of 10 ml were collected. Klainetin B was present in fractions 10 to 14. After concentration in vacuo and freeze-drying, 38 mg of klainetin B were obtained:

ESI+MS: 393.3 Da(M+H)$^+$, ESI−MS: 391.5 Da(M−H)$^−$

EXAMPLE 7

Characterization of Klainetin B

Appearance: light yellow substance, soluble in polar organic solvents but only slightly soluble in water. The compound was stable in a neutral and mildly acidic environment but unstable in the alkaline range. UV maxima: 215 (Sh), 348 nm in water/acetonitrile (8:2), pH 2 and 219 (Sh), 302 and 385 nm in water/acetonitrile (8:2), pH 7. High-resolution mass spectrometry found the following molecular mass for (M+H)$^+$: 393.13391 Da, corresponding to the klainetin B molecular formula of $C_{23}H_{20}O_6$. Electron spray ionization (ESI, positive) produced by means of MS/MS fragmentation the following ions: 393, 289, 283, 271, 131 and 123 Da. Electron spray ionization (ESI, negative) produced by means of MS/MS fragmentation the following ions: 391, 281, 269 and 109 Da.

Klainetin B has the molecular formula $C_{23}H_{20}O_6$, the molecular mass is 392.41 Da.

NMR Signals: See Table 2

TABLE 2

NMR chemical shifts of klainetin B, c = 4 mg/ml, 300 k in DMSO

| Position | δ ($^{13}$C) | m ($^{13}$C) | δ ($^1$H) | $^n$J$_{CH}$ | $^n$J$_{HH}$ |
|---|---|---|---|---|---|
| 2 | 141.50 | d | 7.714 | 7.73 | 7.961 |
| 3 | 127.49 | D | 7.961 | 7.714 | 7.714 |
| 4 | 191.59 | s | — | 7.961, 7.714, 6.16 | — |
| 4a | 104.55 | s | — | 6.16, 14.47 | — |
| 5 | 165.05 | s | — | 14.47, 3.73 | — |
| 5-OH | — | — | 14.47 | — | — |
| 6 | 106.08 | s | — | 6.16, 3.73, 14.47 | — |
| 7 | 163.78 br | s | — | 6.16, 3.73 | — |
| 7-OH | — | — | ? | — | — |
| 8 | 91.18 | d | 6.16 | (3.92) | — |
| 8a | 160.99 | S | — | 3.92, 6.16 | — |
| 9 | 134.99 | s | — | 7.96, 7.714, 7.47 | — |
| 10 2C | 128.31 | d | 7.73 | 7.73, 7.46 | 7.47 |
| 11 2C | 129.01 | d | 7.47 | 7.47 | 7.73 |
| 12 | 130.22 | d | 7.46 | 7.73 | — |
| 15 | 21.60 | t | 3.73 | 6.15 | — |
| 16 | 127.50 | s | — | 6.43, 3.73 | — |
| 17 | 142.84 | s | — | 3.73, 6.57, 6.43, (6.15), (9.09) | — |
| 17-OH | — | — | 9.09 s br | — | — |
| 18 | 144.60 | s | — | 6.57, (6.15), (3.73) | — |
| 19 | 112.65 | d | 6.57 | 6.15, (3.73) | 6.43 |
| 20 | 118.24 | d | 6.43 | — | 6.57, 6.15 |
| 21 | 118.37 | d | 6.15 | 6.57, 3.73 | 6.43 |

EXAMPLE 8

Cytostatic Efficiency Study (IC$_{50}$ Determination)

The cytostatic activities were determined by using purified enzymes in 384-well microtiter plates (coated FlashPlates, NEN Life Science). The enzyme activities were determined by means of phosphorylation of specific peptide substrates. A klainetin dilution series prepared beforehand, with concentrations of 100, 50, 25, 12.5, 6.25, 3.125, 1.5625, 0.7813, 0.3906, 0.195, 0.094, 0.047 and 0 μM, were pipetted into the wells in the appropriate order. The reaction mixture (radiolabeled ATP, buffer solution pH 7.4 and enzyme solutions) was then added followed by incubation at room temperature for 1 h.

Description of CDK4 reaction mixture:

Kinase buffer: 50 mM HEPES, 10 mM MgCl$_2$, 2.5 mM EGTA pH8.0, 10 mM β-glycerol phosphate, 1 mM orthovanadate, 1 mM sodium fluoride, and 1 mM DTT Biotinylated peptide substrate for FlashPlate coating (1 mg/ml solution in PBS buffer)

ATP solution: 100 μCi/ml 33P-γ-ATP and 10 μM ATP

Cyclin D1/CDK4 enzyme solution: 100 mg/ml in kinase buffer

Wash solution: 3% phosphoric acid

Final volume: 50 μl

30 μl of diluted klainetin solution, 20 μl of ATP/enzyme solution (final conc. 1 μCi 33P-γ-ATP, 2 μM ATP and 1 μg of enzyme)

Incubation at room temperature for 2 h, followed by washing 3× with 80 μl of wash solution and measurement in MicroBeta Counter (Wallac), 30 sec.

Description of KDR reaction mixture:

Kinase buffer: 50 mM MOPS, pH7.4, 10 mM MgCl$_2$, 2 mM DTT, 2.5 mM EGTA, 10 mM β-glycerol phosphate, 1 mM orthovanadate, and 1 mM sodium fluoride Peptide substrate: PLCγ1

ATP solution: 25 μCi/ml 33P-γ-ATP und 12.5 μM ATP

KDR enzyme solution: 3.5 μg/ml in kinase buffer

Wash solution: PBS (without Mg$^{2+}$, Ca$^{2+}$)

Final volume 50 μl

10 μl diluted klainetin solution

20 μl of enzyme solution (3.5 μg/ml; 70 ng/well)

20 μl of ATP solution (final concentration 0.5 μCi and 5 μM ATP/well)

Incubation at room temperature for 1 h, followed by washing 3× with 75 μl of wash solution and measurement in MicroBeta Counter (Wallac) for 30 sec.

The activity of the kinases (CDK4 or KDR) was meaured by incorporation of radioactive phosphate from ATP into the substrate and the inhibitory action of the klainetins ($IC_{50}$) was calculated.

$IC_{50}$ values of klainetins A and B

| Compound | $IC_{50}$ CDK4 (μg/l) | $IC_{50}$ CDK4 (μM/l) | $IC_{50}$ CDK2 (μg/ml) | $IC_{50}$ CDK2 (μM/l) | $IC_{50}$ KDR (μg/l) | $IC_{50}$ KDR (μM/l) |
|---|---|---|---|---|---|---|
| Klainetin A | 0.82 | 2.09 | 8.45 | 21.53 | 2.73 | 6.96 |
| Klainetin B | 0.45 | 1.14 | 2.37 | 6.04 | 2.54 | 6.48 |

What is claimed is:

1. A compound of formula I

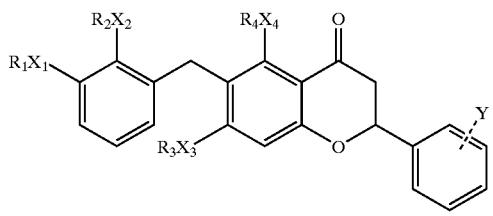

and/or formula II

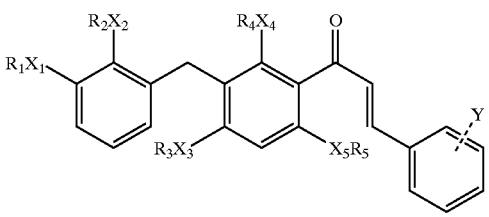

wherein $R_1$, $R_2$, $R_3$, $R_4$ and $R_5$ independently of one another are H, $C_1$–$C_6$-alkyl, $C_2$–$C_6$-alkenyl or $C_2$–$C_6$-alkynyl, unsubstituted or substituted with one or more OH;

$X_1$, $X_2$, $X_3$, $X_4$ and $X_5$ independently of one another are O, NH, N—$C_1$–$C_6$-alkyl, N—$C_2$–$C_6$-alkenyl, N—$C_2$–$C_6$-alkynyl, acyl, aryl or S;

Y is one or more H, halogen, OH, O—$C_1$–$C_6$-alkyl, O—$C_2$–$C_6$-alkenyl, O—$C_2$–$C_6$-alkynyl, $NH_2$, NH—$C_1$–$C_6$-alkyl, NH—$C_2$–$C_6$-alkenyl, NH—$C_2$–$C_6$-alkynyl, NH-acyl, SH, S—$C_1$–$C_6$-alkyl, S—$C_2$–$C_6$-alkenyl, S—$C_2$–$C_6$-alkynyl, acyl or aryl;

wherein the compound may be in any stereochemical form, mixtures of said form(s) in any ratio, physiologically tolerated salts, and/or chemical equivalents thereof.

2. The compound of the formula I or II as claimed in claim 1, in which $X_1$, $X_2$, $X_3$ and $X_4$ independently of one another are O, NH or S, and $R_1$, $R_2$, $R_3$, $R_4$ and $R_5$ independently of one another are H or $C_1$–$C_6$-alkyl, and physiologically tolerated salts and chemical equivalents thereof.

3. A compound of the formula IA

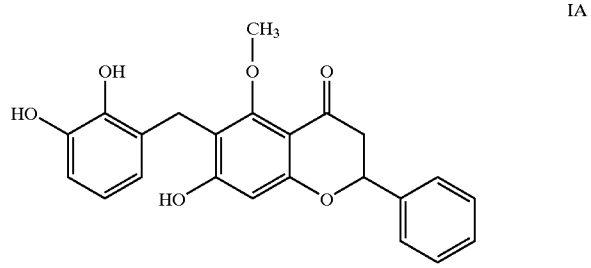

in all stereochemical forms, mixtures of said forms in any ratio, physiologically tolerated salts, and chemical equivalents thereof.

4. A compound of the formula IIA

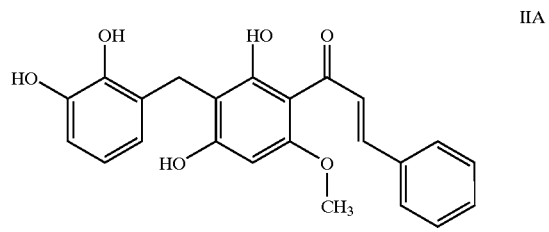

in all stereochemical forms, mixtures of said forms in any ratio, physiologically tolerated salts, and chemical equivalents thereof.

5. A compound of the formula I as claimed in claim 1, wherein the compound is obtained by
 a) extracting the plant *Uvaria klaineri* or one of its variants or mutants, or growing the plant *Uvaria klaineri* until a compound of formula IA accumulates in the plant,
 b) subsequently isolating the compound, and
 c) where appropriate, converting the compound into chemical equivalents and/or physiologically tolerated salts thereof.

6. A compound of the formula II as claimed in claim 1, wherein the compound is obtained by
 a) extracting the plant *Uvaria klaineri* or one of its variants or mutants, or growing the plant *Uvaria klaineri* until a compound of formula IIA accumulates in the plant,
 b) subsequently isolating the compound, and
 c) where appropriate, converting the compound into chemical equivalents and/or physiologically tolerated salts thereof.

7. A method for preparing a compound of formula I and/or II or a physiologically tolerated salt thereof as claimed in claim 1, which comprises the steps of
 a) culturing the plant *Uvaria kaineri* or one of its variants or mutants under suitable conditions in a culture medium, until a compound of formula IA and/or IIA accumulates in the plant,
 b) subsequently isolating the compound or compounds from the plant material, and
 c) where appropriate, converting said compound or compounds into chemical equivalents and/or physiologically tolerated salts thereof.

8. The method as claimed in claim 7, wherein the plant is cultured under tropical or subtropical conditions.

9. A pharmaceutical comprising at least one compound of formula I or a physiologically tolerated salt thereof as claimed in any one of claims 1, 2 and 3.

10. A pharmaceutical comprising at least one compound of formula II or a physiologically tolerated salt thereof as claimed in any one of claims 1, 2 and 4.

11. A method for the inhibition of cyclin-dependent kinases (CDK), comprising administration of the pharmaceutical as claimed in claim 9.

12. A method for the inhibition of cyclin-dependent kinases (CDK), comprising administration of the pharmaceutical as claimed in claim 10.

13. A method for regulation of cell growth comprising administration of the pharmaceutical as claimed in claim 9.

14. A method for regulation of cell growth comprising administration of the pharmaceutical as claimed in claim 10.

15. A method for producing pharmaceutical preparations, which comprises the steps of
   a) isolating at least one compound of the formula I or a physiologically tolerated salt thereof as claimed in claim 1, 2, or 3 and
   b) combining the compound(s) with suitable excipients and/or carriers.

16. A method for producing pharmaceutical preparations, which comprises the steps of
   a) isolating at least one compound of the formula II or a physiologically tolerated salt thereof as claimed in claim 1, 2, or 4, and
   b) combining the compound(s) with suitable excipients and/or carriers.

* * * * *